(12) United States Patent
Ogawa

(10) Patent No.: US 11,193,753 B2
(45) Date of Patent: Dec. 7, 2021

(54) TOMOGRAPHIC IMAGE IMAGING DEVICE

(71) Applicant: Hiroshi Ogawa, Yokohama (JP)

(72) Inventor: Hiroshi Ogawa, Yokohama (JP)

( * ) Notice: Subject to any disclaimer, the term of this patent is extended or adjusted under 35 U.S.C. 154(b) by 0 days.

(21) Appl. No.: 16/631,860

(22) PCT Filed: Jul. 18, 2018

(86) PCT No.: PCT/JP2018/026936
§ 371 (c)(1),
(2) Date: Jan. 17, 2020

(87) PCT Pub. No.: WO2019/017392
PCT Pub. Date: Jan. 24, 2019

(65) Prior Publication Data
US 2020/0158490 A1 May 21, 2020

(30) Foreign Application Priority Data

Jul. 19, 2017 (WO) .................. PCT/JP2017/026091

(51) Int. Cl.
*G01B 9/02* (2006.01)
*A61B 5/00* (2006.01)
*G01B 11/24* (2006.01)

(52) U.S. Cl.
CPC ........ *G01B 9/02091* (2013.01); *A61B 5/0066* (2013.01); *G01B 11/2441* (2013.01); *A61B 2562/0233* (2013.01)

(58) Field of Classification Search
CPC ............ G01B 9/02091; G01B 11/2441; A61B 5/0066
See application file for complete search history.

(56) References Cited

U.S. PATENT DOCUMENTS

| | | | | |
|---|---|---|---|---|
| 2004/0233944 | A1* | 11/2004 | Dantus | G01B 9/02091 372/25 |
| 2007/0014464 | A1* | 1/2007 | Ohashi | A61B 3/102 382/131 |
| 2011/0306867 | A1* | 12/2011 | Gopinathan | A61B 5/064 600/407 |

FOREIGN PATENT DOCUMENTS

| | | | | |
|---|---|---|---|---|
| JP | 2004132939 | A | * 4/2004 | |
| JP | 2007267761 | A | * 10/2007 | ............. A61B 3/102 |

OTHER PUBLICATIONS

Silipigni, Giuseppe et al. "Optimization of the pulse-compression technique applied to the infrared thermography nondestructive evaluation". NDT&E International, No. 87, Feb. 4, 2017, pp. 100-110. (Year: 2017).*

* cited by examiner

*Primary Examiner* — Michael A Lyons
(74) *Attorney, Agent, or Firm* — Sughrue Mion, PLLC

(57) ABSTRACT

A tomographic imaging device includes a light source, a light pulse generator, a wave shaper, a splitter, a frequency shifter, a light path length changer, an optical detector, filters, a demodulator and an analyzer. The light pulse generator generates an optical pulse train from an output of the light source. The wave shaper modulates the optical pulse train by binary phase shift keying with PN codes. The splitter splits the pulse train into two signals, one is shifted by the frequency shifter, and one has a path length changed by the light path length changer. The optical detector inputs back scattered light from an object and the signal whose length has changed, and generates a difference signal. The filters filter the difference signals, and the demodulator demodulates the filter outputs. The analyzer calculates a reflection site of the measurement object by analyzing the output signal of the demodulator.

10 Claims, 16 Drawing Sheets

(A) OPL (OPTICAL PATH LENGTH) ABC − OPL ADE=2r=0

Figure 1:
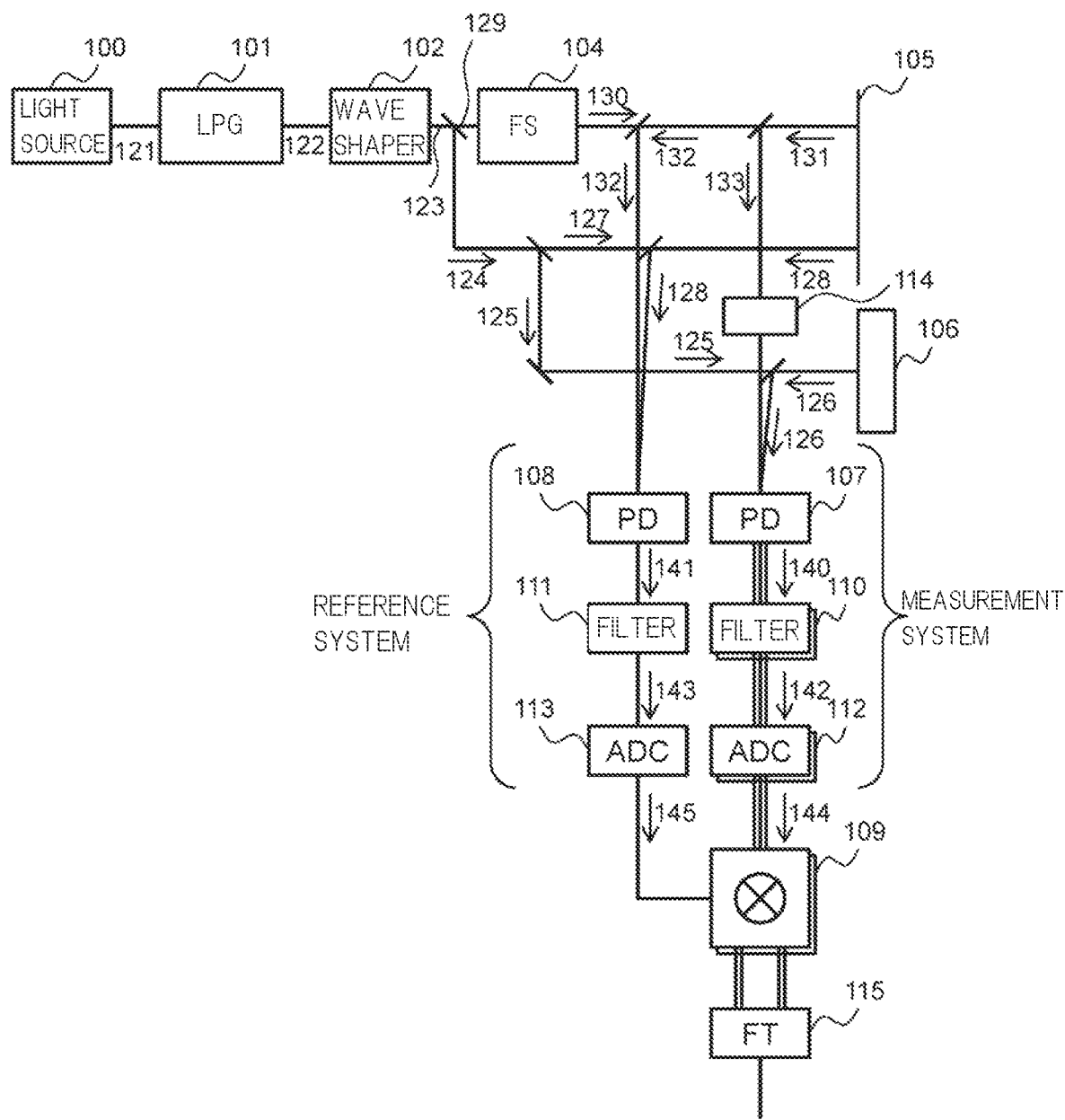

FREQUENCY : SHIFT FREQUENCY (B) −CT<OPL ABC − OPL ADE=2r<CT $$S_n = S(n \cdot \omega_s)$$

(C) OPL ABC − OPL ADE=2r<−CT, CT<OPL ABC − OPL ADE=2r

FILTER OUTPUT:ZERO

TOMOGRAPHIC IMAGE IMAGING DEVICE

CROSS REFERENCE TO RELATED APPLICATIONS

This application is a National Stage of International Application No. PCT/JP2018/026936, filed Jul. 18, 2018, claiming priority to International Patent Application No. PCT/JP2017/026091, filed Jul. 19, 2017, the entire contents of each of which are herein incorporated by reference in their entireties.

TECHNICAL FIELD

This invention is related to tomographic image imaging devices, and more specifically tomographic image imaging devices using codes which repeat with a predetermined interval such as M-sequence codes (for example, repeated pseudorandom noise, codes with autocorrelation characteristics).

BACKGROUND

The following prior techniques are shown as the background of this technical field. In the patent document 1 (JP 2011-117789 A), an optical coherence tomographic device is shown which contains: a wideband optical pulse generation unit which generates wideband optical pulse of predetermined range of wavelength; an optical pulse An optical pulse demultiplex-delay-multiplex unit which demultiplexes above wideband optical pulse into optical pulses with bandwidth narrower than above predetermined range of wavelength, multiplexes the above narrowband optical pulses after delaying with different intervals, and generates an optical pulse train made of multiple pulses with different center wavelengths; an optical divider which divides above optical pulse train into a measurement optical pulse train and a reference optical pulse train; an optical pulse irradiation/capture unit which irradiates above measurement optical pulse train to the measurement object, and captures the back scattered optical pulse train generated by back scattering of above measurement optical pulse train by above measurement object; an optical combiner which forms a combined optical pulse train by combining above reference optical pulse train and above back scattered optical pulse train; an optical pulse intensity measurement unit which measures optical intensity of each optical pulse of above combined optical pulse train; and a tomographic image deriving unit which Fourier transforms the above optical intensity measurement data as a function of wave number of each pulse of above optical pulse train, and derives a tomographic image of above measurement object based on Fourier transformed above measurement data.

In addition, in the patent document 2 (JP 2006-184284 A), a light source of an optical coherence tomographic device with a measure to change wave number in a stepwise manner is described.

Furthermore, in an optical coherence tomography described in the patent document 3 (JP 2007-267761 A), the light emission block emits near infrared coherent light with different wavelengths from light source to the light interference block. The beam splitter of the light interference block makes the light direct to the optic fundus while partially reflects the light to optical wave length shifter. The shifter modulates the light frequency according to the oscillation signal S and modulates again the frequency of the light reflected by a movable mirror. Then, the beam splitter makes interfere the measurement light and the reference light reflected by the mirror and emits the interfered light to the light detection block. The light detection block receives the interfered light, demodulates the detected signal representing the light intensity of above interfered light with the use of oscillation signal S, and filters the high-frequency components. The light detection block further calculates the cross-sectional shape and oxygen saturation SO2 of the optic fundus.

PRIOR TECHNICAL DOCUMENTS

Patent Documents

Patent Document 1: JP 2011-117789 A
Patent Document 2: JP 2006-184284 A
Patent Document 3: JP 2007-267761 A

SUMMARY OF INVENTION

Problem Solving by Invention

In aforementioned optical coherence tomographic devices, light pulse is irradiated to measurement object and captures light the scattered by the measurement object. For this reason, the difference of attenuation is large within pulse width, i.e., scattered light is intense from the part near the emission side and is weak from the deeper part. This makes difficult to acquire the clear tomographic image through the predetermined depth. In particular, with wider irradiation pulse and with deeper imaging range, the ratio of the intensity of direct light containing image information between shallower and deeper parts is large, making reflected direct light from the deeper parts masked by reflected direct light from the shallower parts.

In addition, it is desired to improve the resolution in the depth (slice width) and to obtain tomographic images with high resolution and high signal/noise ratio. For this purpose, light pulse widths have to be smaller. The optical characteristic of biological tissues shows small degree of attenuation but strong scattering; the intensity of the straight light severely and exponentially declines due to the scattering characteristic. Scattering characteristic is different depending on type of tissues, and the decline of straight light ranges between 20 dB to 50 dB per 1 mm. As stated later, the pulse width determines target range of depth. In the patent document 3, however, spectrally-spread driving signal (modulated driving signal) drives (makes emit) laser light source 14; it is difficult to decrease light pulse width because of the speed limit of the transistor operation used in the electrical circuits. For example, considering the generation of 10 ps pulse by electrical circuits, 10 ps cycle corresponds to 100 GHz; as pulse-like waveforms have to contain a number of higher harmonics, transistors have to operate more rapidly and it is impossible to generate such pulses by electrical circuits.

Furthermore, the straight traveling light has stable phase wavefronts in its traveling direction; these contain effective image information. On the other hand, as scattering lights reach light receiver via various light paths, coherent lengths are disrupted and irregular, and become noise. Therefore, the noise energy arising from scattering lights is small if depth range is small.

For these reasons, if depth range is predetermined by the degree of straight light decay, such that the ratio of decay between shallower and deeper parts is predetermined as 30 dB and the decay rate within the observed tissues is 20 dB/mm, the depth range is 1.5 mm. Pulse width corresponding to depth range of 1.5 mm is 1.5 mm×2/(3×10$^{-11}$)=10 ps. The shorter this width is, the better the signal/noise ratio is.

In other attempts, improvement in resolution using codes with long symbol length is investigated; the measurement time, however, becomes longer to gather weak reflection lights. Especially, as living bodies move with pulsation etc., problems of unclear images occur with longer measurement time.

This invention aims to propose a tomographic imaging device which obtains high-resolution high-signal/noise ratio tomographic image of deep part of measurement object in short measurement time by irradiating measurement object with light pulse signal, light generated by light source and directly modulated by spreading codes.

Measures to Solve Problem

The following shows a representative example of an invention disclosed in this application. That is, a tomographic imaging device characterized by containing a light source emitting a coherent light; a generator which generates an optical pulse train with coherent carrier and spatial length of pulse width shorter than target observation region of measurement object by binary phase shift keying light emitted by above light source with PN codes having autocorrelation characteristic of low interference between neighboring waves; a frequency shifter which changes the frequency of optical pulse train modulated by above generator; a light path length changing part which changes the light path of the optical pulse train with frequency changed by above frequency shifter; an optical detection part which inputs back scattered waves from above measurement object irradiated by both the optical pulse train output by light path length changing part and the optical pulse train output by above generator; a filter which extracts the difference signal of shift frequency of above frequency shifter from output of above optical detection part; a demodulator which combines the difference signal extracted by above filter and the reference signal synchronized with the shift frequency of above frequency shifter; and an analyzing part which analyzes the output signal of above demodulator; and by above analyzer calculating the reflection site of the measurement object by analyzing the output signal of above demodulator.

Effect of Invention

By an embodiment of this invention, tomographic images are taken in deep part of measurement object with high resolution and high signal/noise ratio (SNR) in a short time.

SIMPLE LEGENDS OF FIGURES

Figure 2:
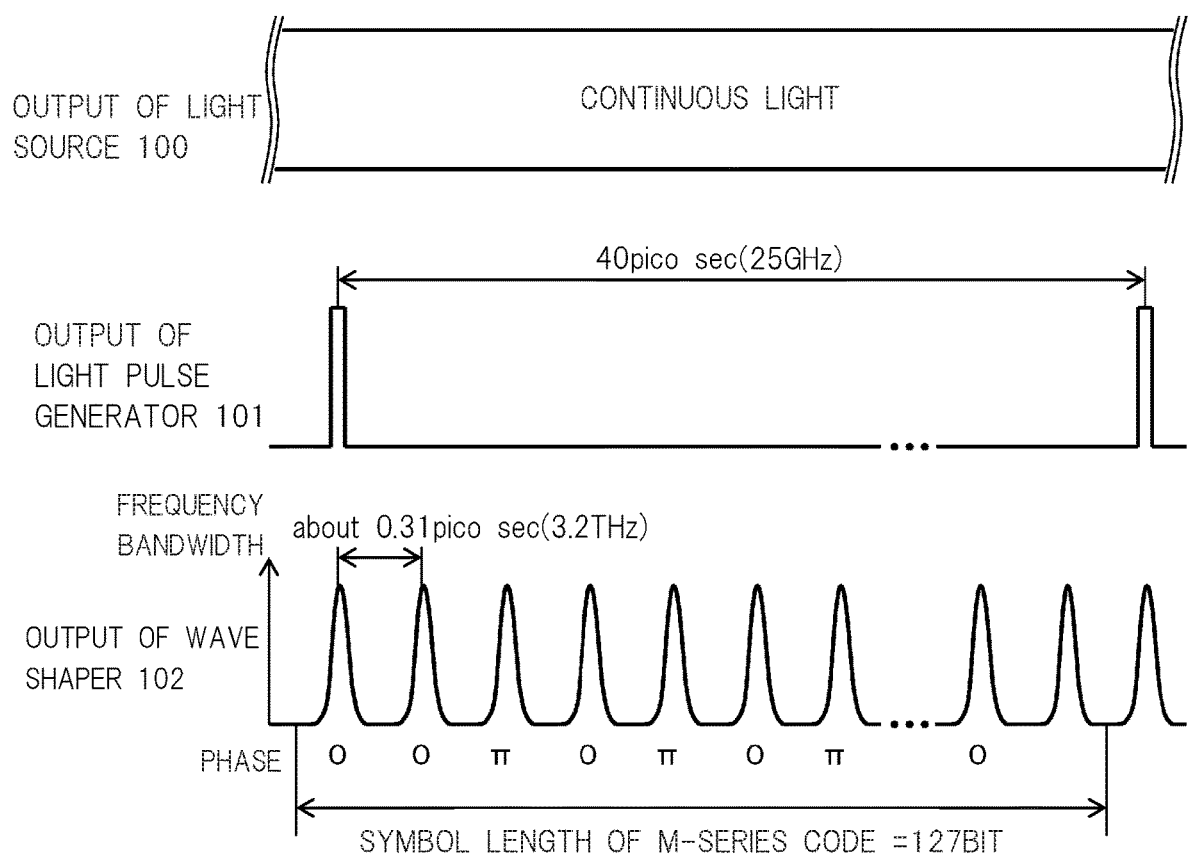
Figure 3:
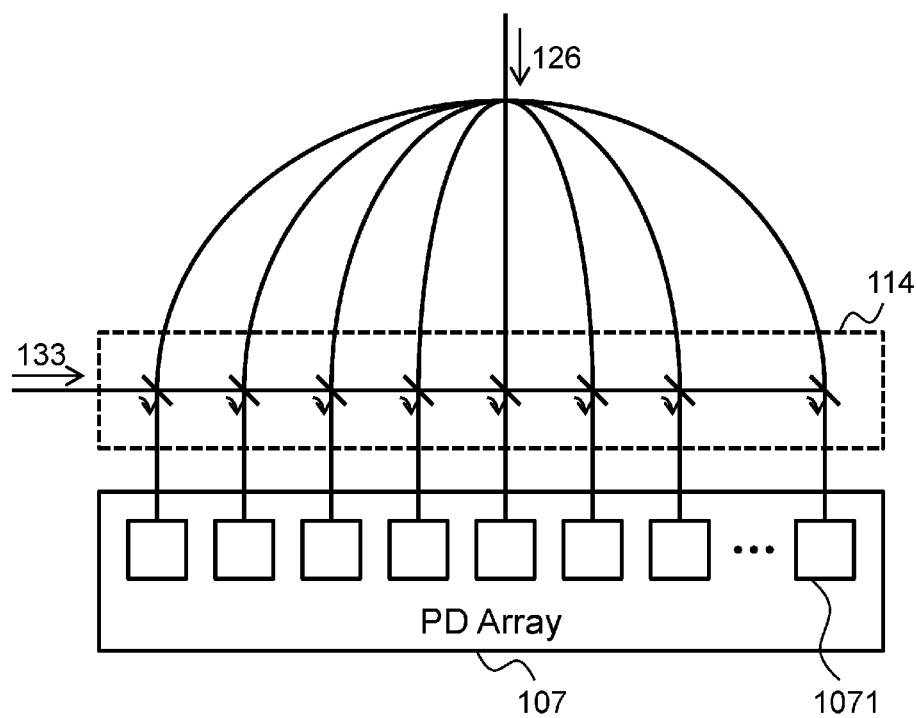
Figure 4:
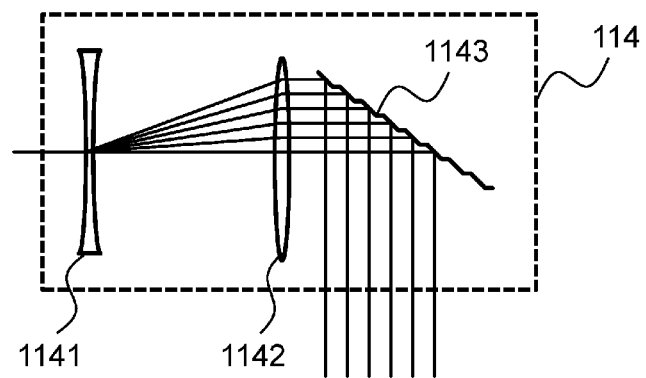
Figure 5:
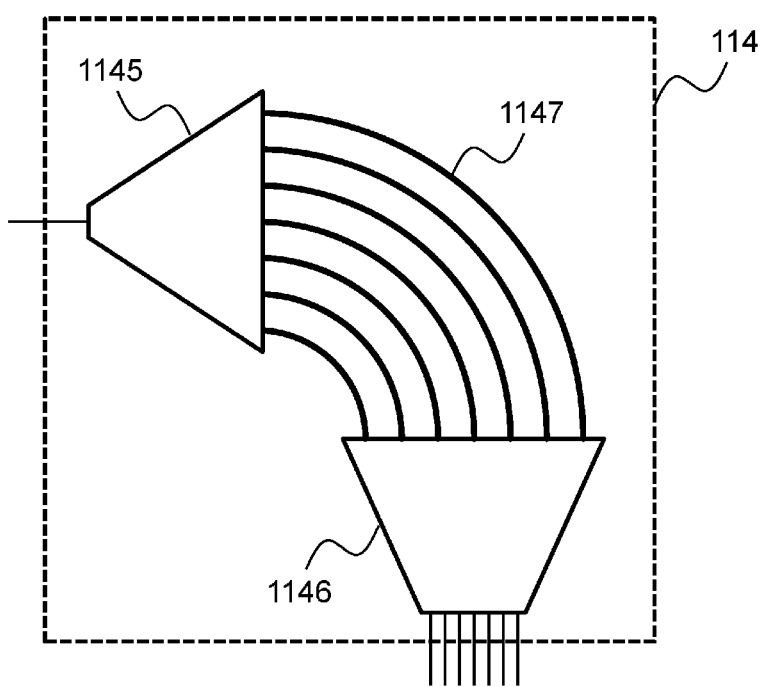
Figure 6:
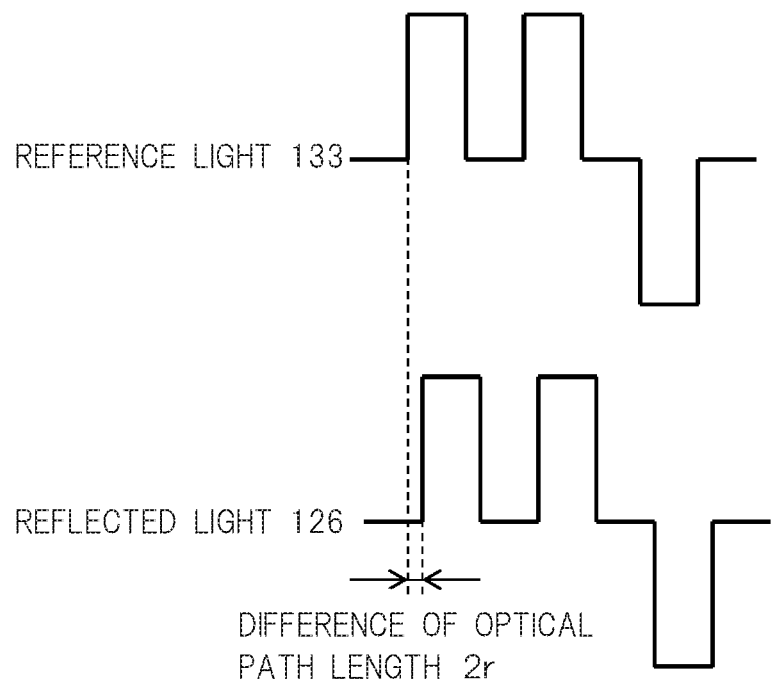
Figure 7:
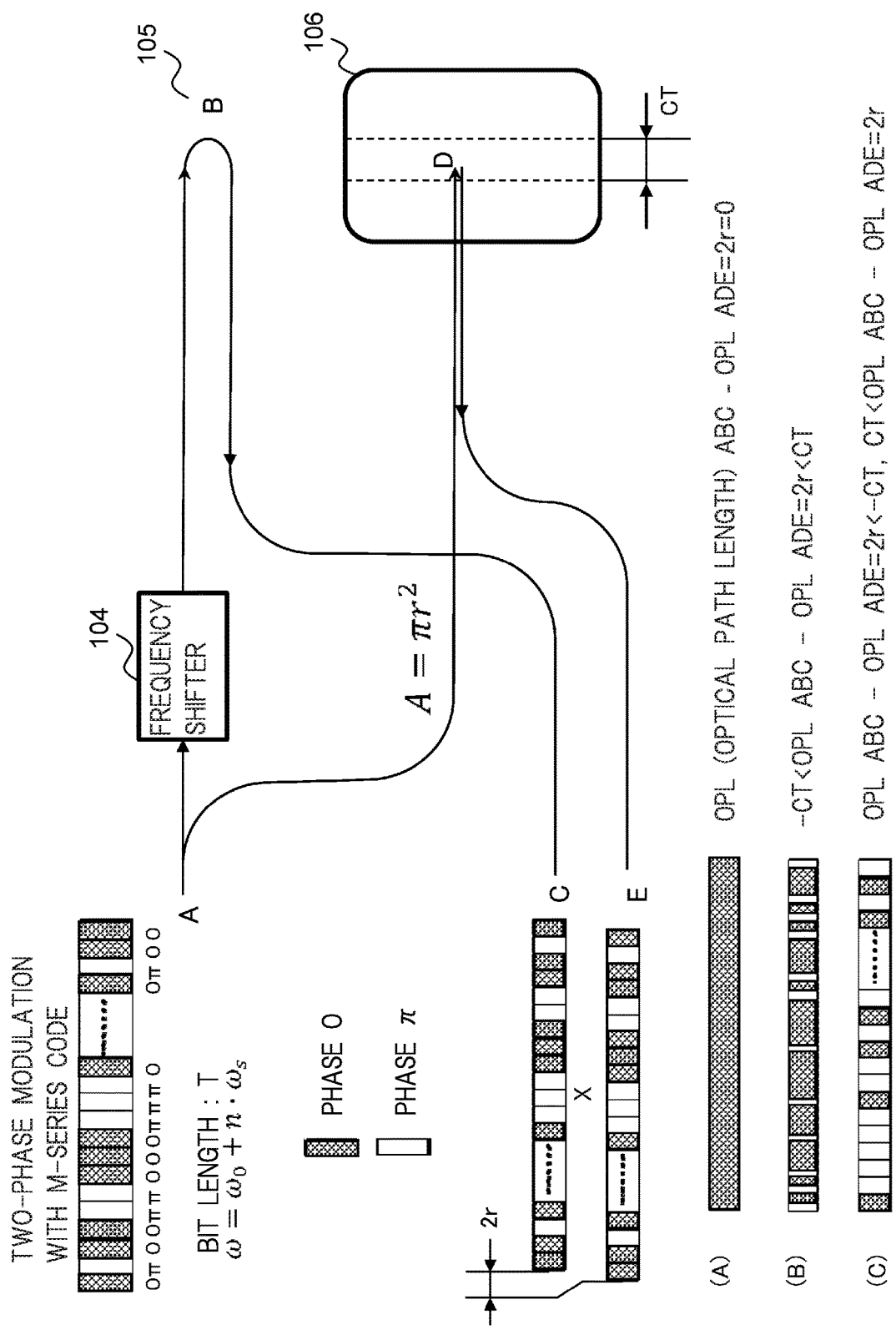
Figure 8:
Figure 8:
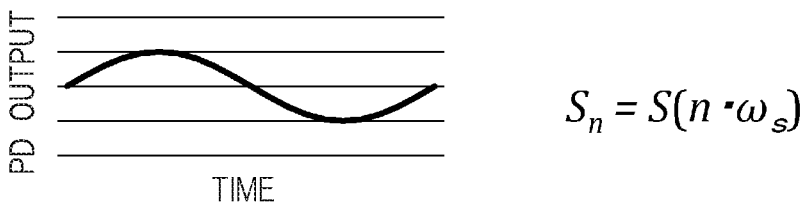
Figure 8:
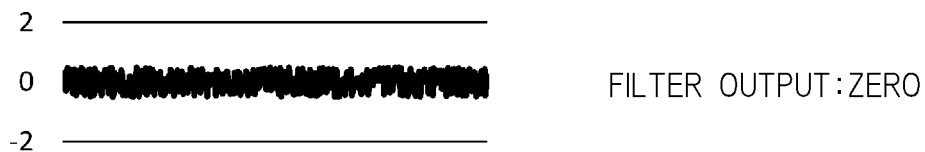
Figure 9:
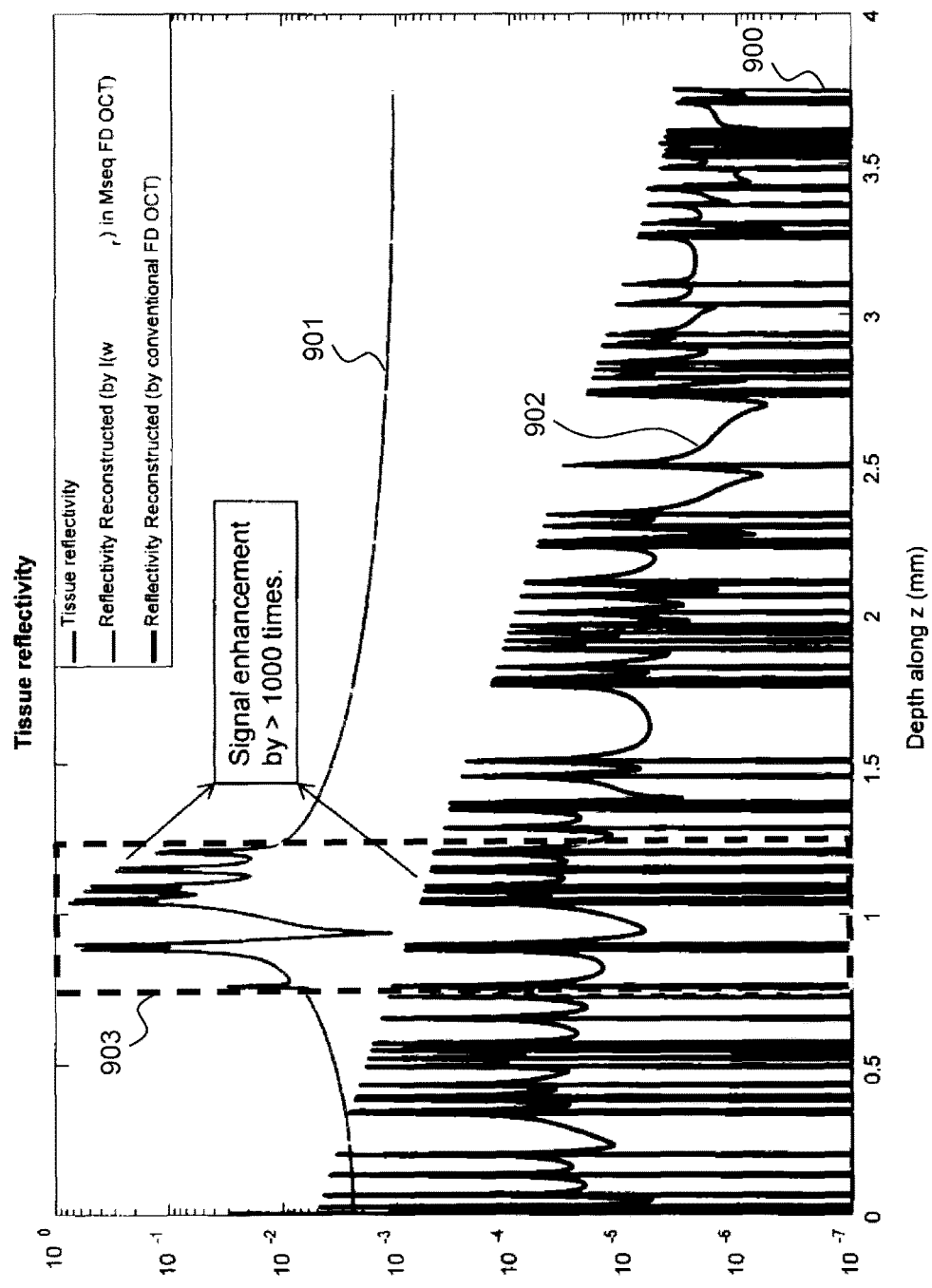
Figure 10:
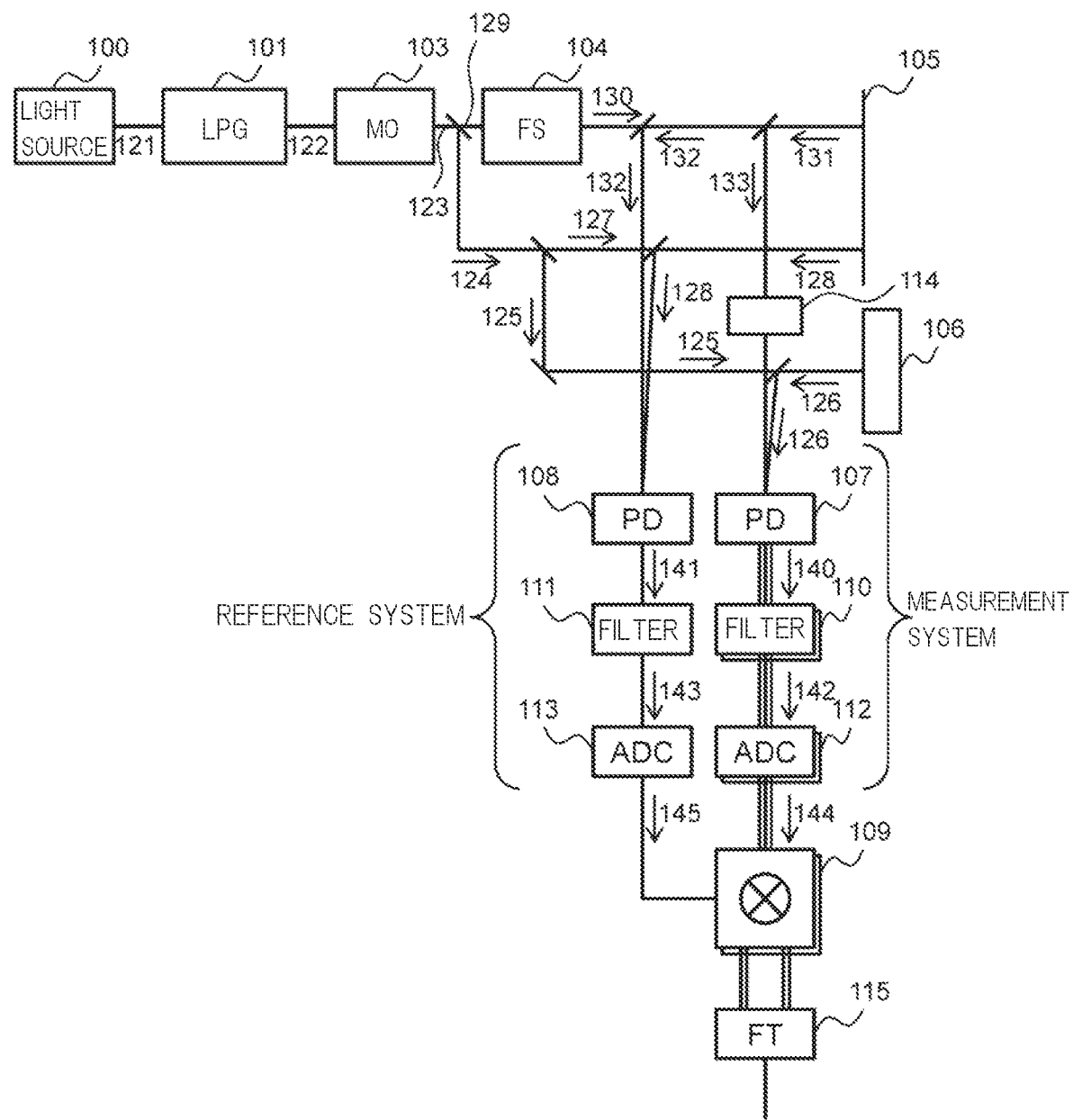
Figure 11:
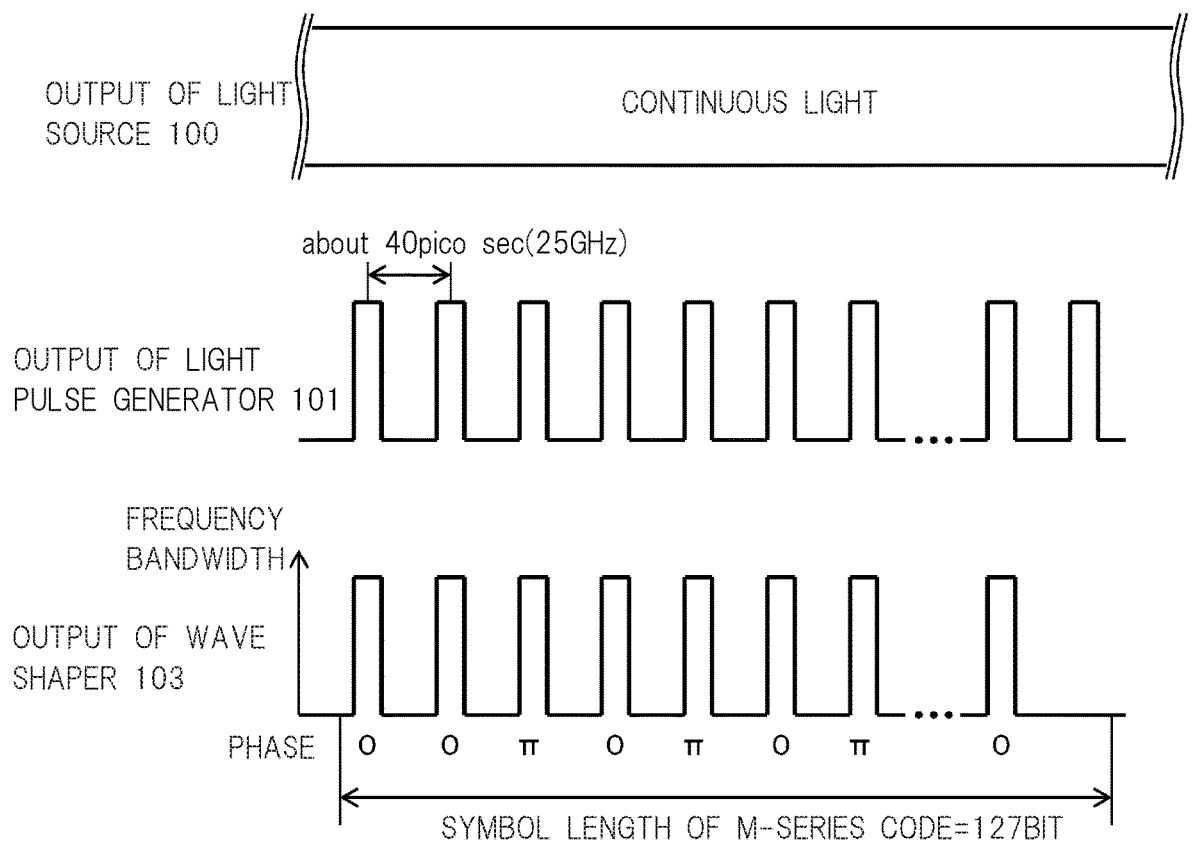
Figure 12:
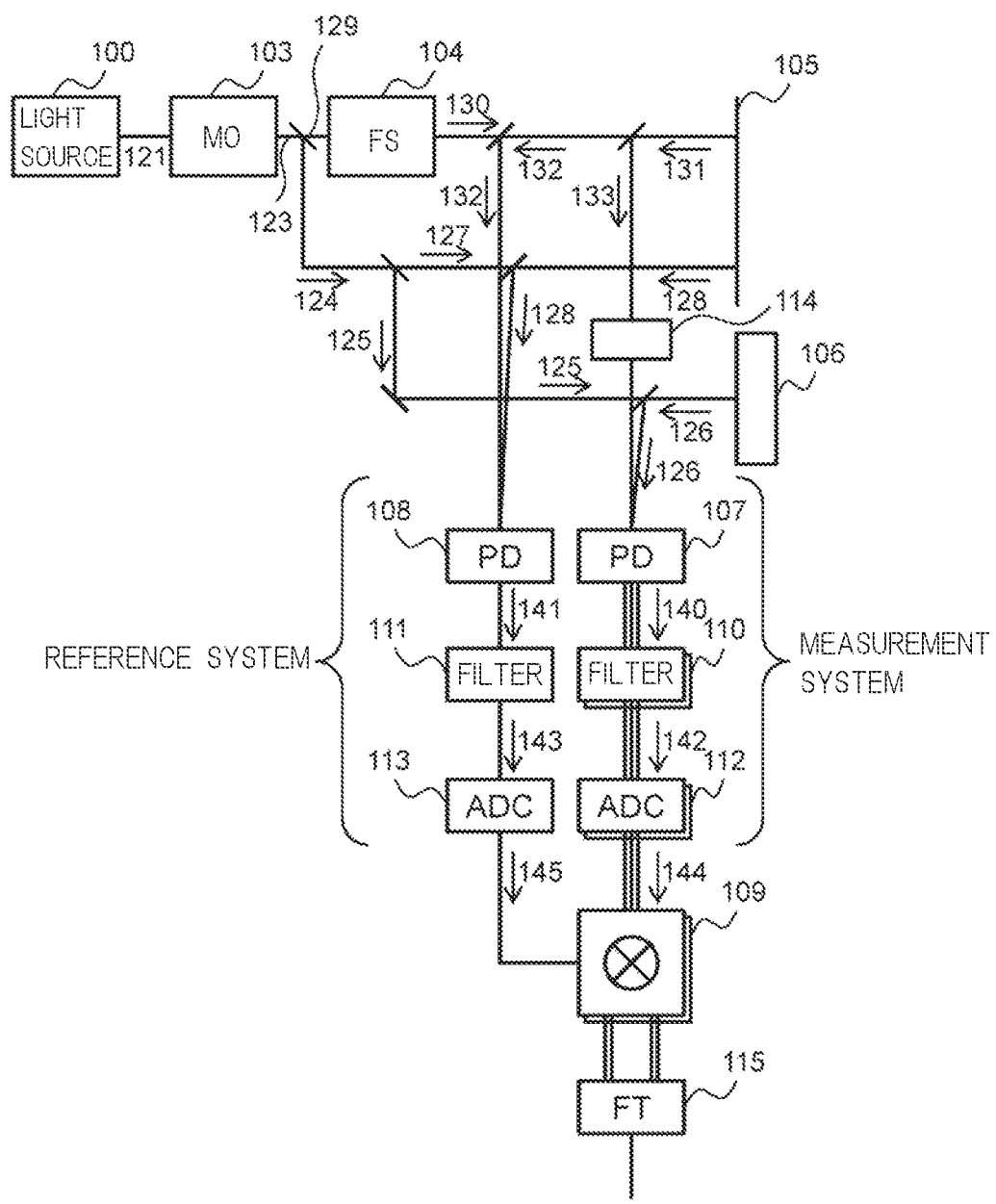
Figure 13:
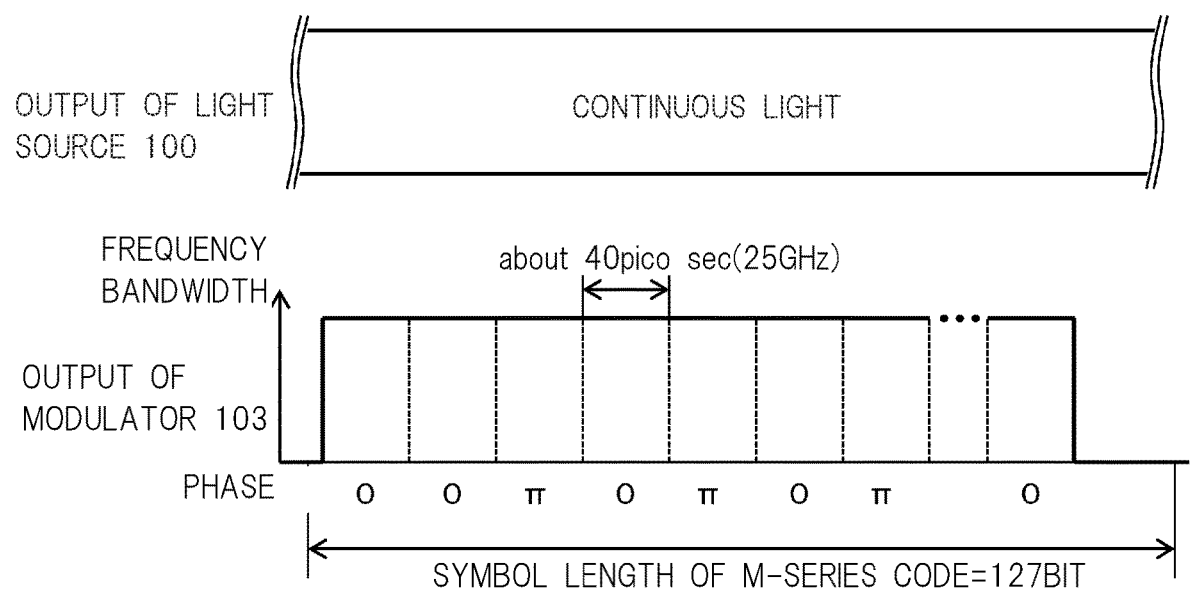
Figure 14:
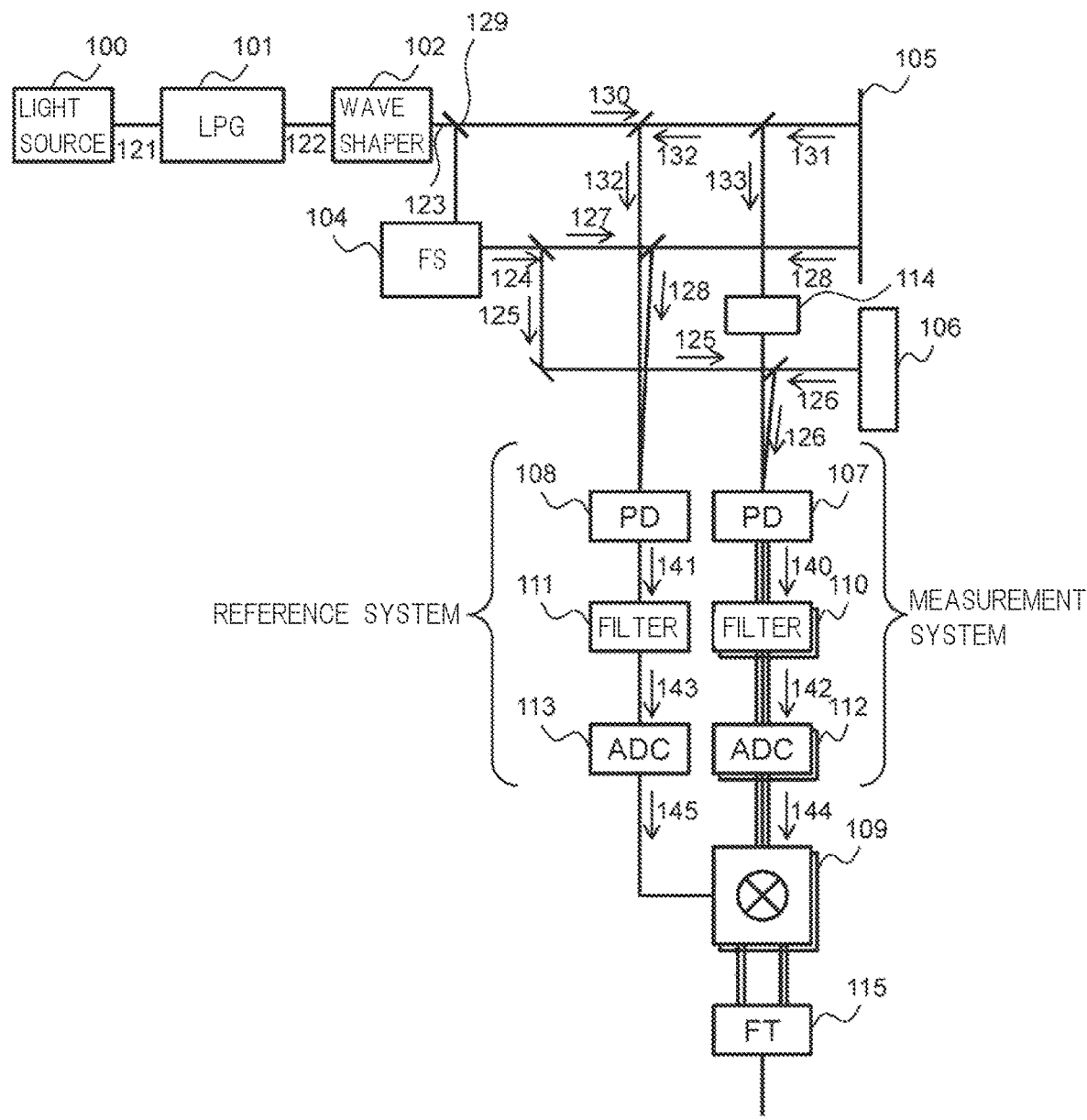
Figure 15:
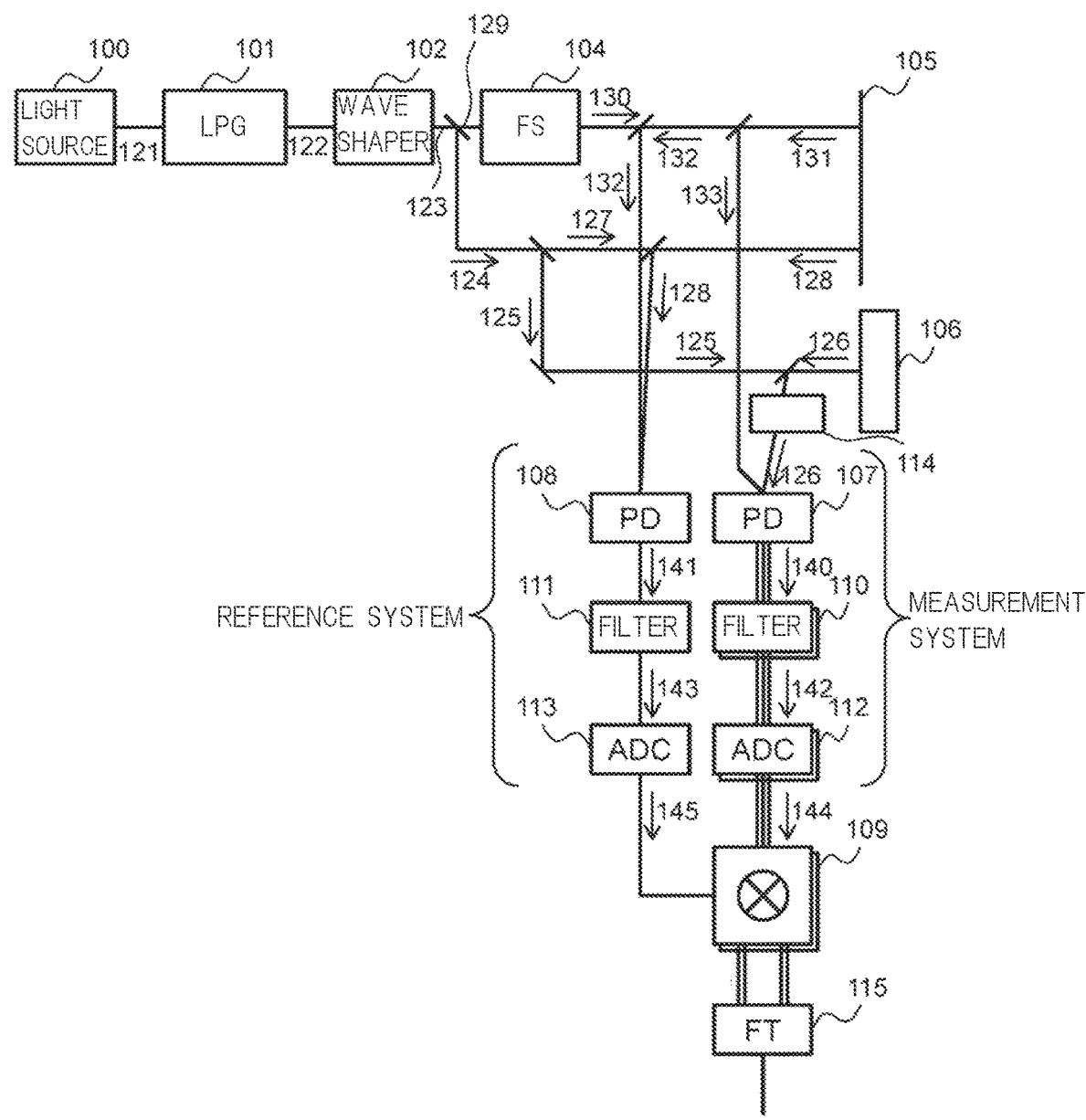
Figure 16:
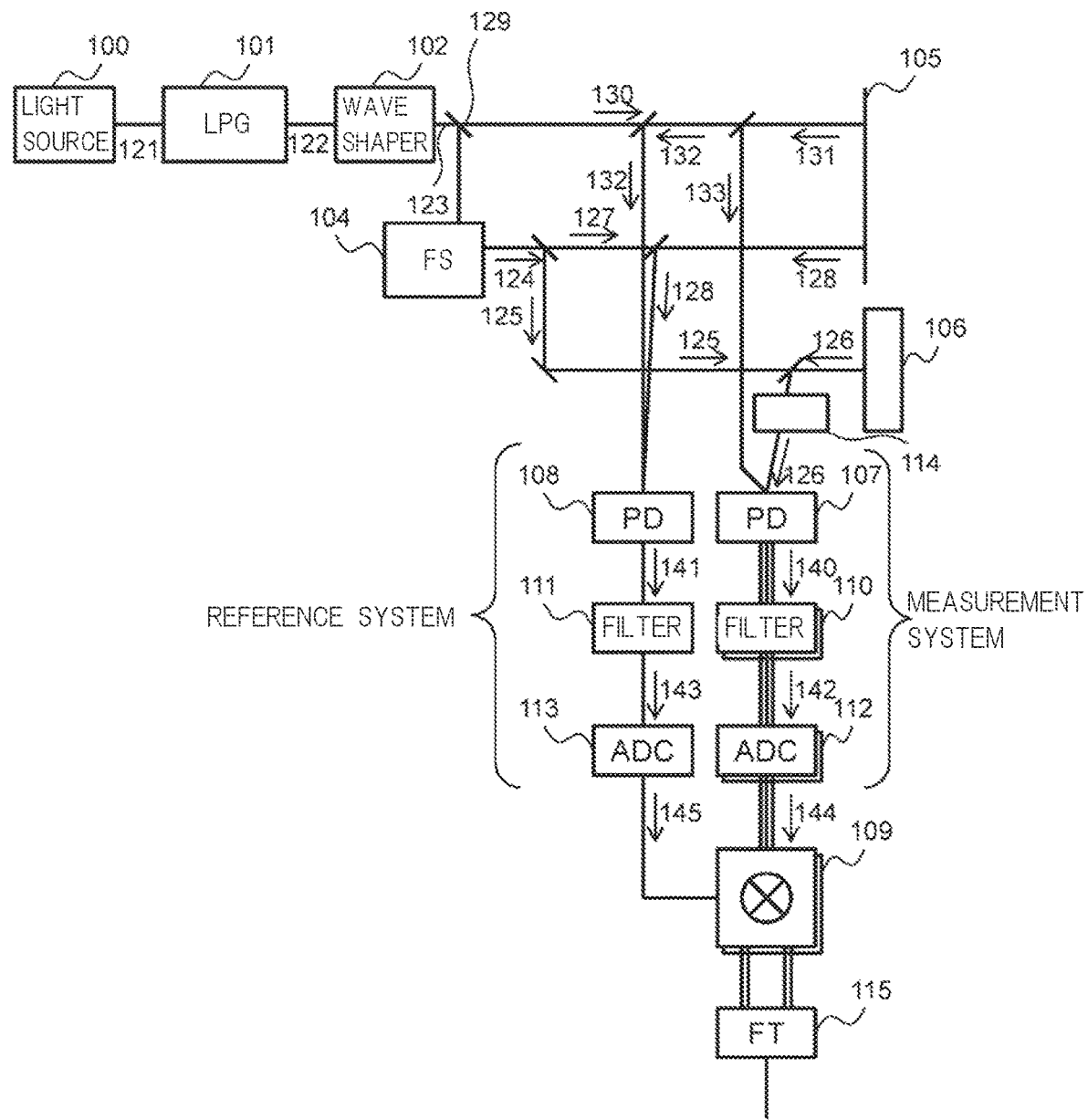

FIG. 1 A figure showing constitution of tomographic imaging device according to the first embodiment FIG. 2 A figure showing an example of optical output from demodulator according to the first embodiment FIG. 3 A figure showing concept of optical detector and light path length changing part FIG. 4 A figure showing an example of constitution of light path length changing part FIG. 5 A figure showing an example of constitution of light path length changing part FIG. 6 A figure showing methods to obtain reflection site and reflection ratio from signals output from optical detector FIG. 7 A figure showing measurement range of reflection site by autocorrelation FIG. 8 A figure showing output signal from optical detector FIG. 9 A figure showing measurement range of tomographic imaging device according to this embodiment FIG. 10 A figure showing constitution of tomographic imaging device according to the second embodiment FIG. 11 A figure showing an example of optical output from demodulator according to the second embodiment FIG. 12 A figure showing constitution of tomographic imaging device according to the third embodiment FIG. 13 A figure showing an example of optical output from demodulator according to the third embodiment FIG. 14 A figure showing a modification example of constitution of tomographic imaging device according to the first embodiment FIG. 15 A figure showing a modification example of constitution of tomographic imaging device according to the first embodiment FIG. 16 A figure showing a modification example of constitution of tomographic imaging device according to the first embodiment

EMBODIMENTS TO IMPLEMENT INVENTION

In the following paragraphs, embodiments of this invention are explained.

First Embodiment

FIG. 1 shows constitution of tomographic imaging device according to the first embodiment of this invention.

The first embodiment of tomographic imaging device contains light source 100, light pulse generator 101, wave shaper 102, frequency shifter 104, light path length changing part 114, optical detector 107, 108, filter 110, 111, AD converter 112, 113, demodulator 109, and Fourier transformer 115.

The light source 100 is a light source emitting coherent continuous light 121, and can be a laser light source for example. In addition, light emitting from light source 100 is regulated to change the wave length within a predetermined wave length range by a predetermined frequency step size. The frequency bandwidth (frequency range) of emitted light from light source 100 corresponds to the image resolution of measurement object 106, and between the light pulse width T and the light pulse interval T1 of output light, measurement site can be separately measured from pulse light generated by output light. That is to say that output light wave length is changed at the step to measure reflection site and reflection intensity from phase and amplitude information of measured reflected waves.

The light pulse generator 101 converts the light (continuous light) generated by light source 100 to pulse light 122 with predetermined width and predetermined waveform. Specifically, light pulse generator 101 is composed of light comb generator and enables to obtain femtosecond width pulse light with constant intervals by excitation of light comb generator with predetermined high-frequency signals of microwave or millimeter wave. For example, by controlling by 25 GHz signal, as shown in FIG. 2, femtosecond width pulse light with 40 ps interval is generated. Preferably, pulse width of pulse light 122 may be less than or equal to 10 ps. Incidentally, it is desirable to define pulse light with not by full width at half maximum but by time width to reach zero amplitude.

As the duty ratio of femtosecond width pulse light signal 122 generated by light pulse generator 101 is very small so that pulse light does not interfere with each other and pulse light train with each of independent pulse light is generated. Therefore, the measurement object range is narrow and this enables to decrease the effect of scattered light from the axial direction of light. In addition, the changes in decay within the measurement object range can be small and this enables to obtain clearer image. By these effects, the signal/noise ratio of measurement object 106 is improved.

On the contrary, if the duty ratio of pulse light signal 122 is too small, considering the limit of light intensity peak due to the safety issue, the mean energy of light becomes small resulting in shallower detectable depth when irradiated to measurement object 106 or in longer measurement time with increased number of integration for each measurement site.

Wave shaper 102 reshapes the light pulse signal 122 which is the output from light pulse generator 101 and repeats with a constant interval, and outputs needed number of pulses of duplicated signal at needed time points. In addition, similarly, needed number of pi-phase pulses of duplicated signal but with reversed phase and the same envelope are output at needed time points. By these functions, wave shaper 102 generates M-series code of symbol length $2^{n-1}$ and outputs signal 123.

In this embodiment, wave shaper 102 spectrally decomposes input signal 122 with spectroscope, adjusts the phase and amplitude of each spectrum with spatial light modulator, and again combines these spectra to generate and output the predetermined M-series code. By this, a fixed M-series code signal is repeatedly generated and output. Spatial light modulator enables rapid modulation and enables to set pulse width corresponding to 1 bit of M-series code to a predetermined value, making possible to set measurement object range to a predetermined range. Though the predetermined measurement range depends on the light attenuation and scattering characteristics within the target, it is desirable to get sufficient signal/noise ratio in all predetermined range. In actual biological measurements, measurement object range determined by 1-bit pulse is requested to be smaller than or equal to about 0.5 mm.

As shown in FIG. 2, the spatial light modulator exemplified in this embodiment outputs signal 123, i.e., reshaped signal of light pulse signal duplicated by wave shaper 102 into the predetermined wave form such as Chebyshev-type wave form. Using Chebyshev-type wave form, side lobes are decreased in the frequency domain and interference between neighboring waves are reduced, and resolution of measurement object 106 is improved. Spatial light modulator may output signal with waveforms other than Chebyshev type if the side lobe of the wave form is sufficiently small.

Wave shaper shown in figures generates 127 pulses (127 codes) within the 40 ps interval, and generates light signal 123 modulated at 3.2 THz. Number of pulses generated from one light pulse by spatial light modulator may not be limited to 127 bits, but may be longer bits of 255 or larger, or shorter bits of 63 or smaller.

Wave shaper 102 constructed with arrayed-waveguide grating (AWG) enables high-speed modulation similarly as spatial light modulator. It is also possible to make a fixed M-series binary phase modulated signal by statically controlling phase and amplitude of spectrum in the frequency domain.

As shown in FIG. 2, neighboring pulses may be separate with zero levels between pulses, or side lobes of neighboring pulses may be connected to make inter-pulse intervals non-zero level.

Signals output from wave shaper 102 divides into signal 124 and signal 129; signal 129 is input into frequency shifter. The other signal 124 further divides into signal 125 and signal 127; signal 127 is reflected by a reference system reflector to become signal 128, and changes direction to be delivered to optical detector 108. Signal 125 is irradiated to measurement target 106, is reflected or scattered at measurement object 106 (for example, back scattered wave), and is introduced to optical detector 107 as signal 126. Reflected light 126 from measurement object 106 contains information of reflection sites within a finite interval. Information of reflection sites outside the finite interval is scattered as very high frequency noise. Reference system reflector may not be necessarily a reflector but may be a functional unit to turnaround signals 130 and 127 to become signals 131 and 128 synchronizing and keeping the same light path lengths with each other. For example, structure to turnaround within a fiber with effective length controllable by external electrical field may be used, with the ability to rapidly change effective length by changes in external electrical field.

Frequency shifter 104 converts the frequency of input signal 128 and outputs signal 130. The frequency-converted signal is combined in optical detector 107, 108 to detect the frequency difference signal 140, 141 as beat signal of shifted frequency shift (refer to FIG. 8(A)). For this purpose, frequency shift is preferably the frequency (for example 100 MHz) which is easy to deal as electrical signal in the process after optical detector 107 and 108. Output signal 130 from frequency shifter 104 is reflected by reference system reflector 105 to be signal 131, and then divided to be signal 133 and partly be derived to optical detector 107. Signal 133 travels through light path length changing part 114 and becomes parallel light signals travelling along different light path lengths (and having different wave fronts), and is introduced to optical detector 107. The other divided signal 132 of reflected signal 131 is introduced to optical detector 108.

In FIG. 1, frequency shifter 104 is placed in the path of light 130 input to reference system reflector 105, but this may be placed in the path of light 124 input to measurement object 106 in measurement system (to also affect light 7 input to reference system reflector 105) as shown in FIGS. 14 and 16. That is, it is only needed that two light inputs to both optical detector 107 and optical detector 108 have frequency difference and that optical detectors 107 and 108 can detect difference frequency (shifted frequency by frequency shifter 107) signal.

Moreover, in FIG. 1, light path changing part 114 is placed in the path of reflected light 133 from reference system reflector 105, but this may be placed in the path of reflected light 126 from measurement object 106 as shown in FIGS. 15 and 16. Light path changing part 114 is, as stated later, the part to change the light input to optical detector 107 into that travelling along plural of light path lengths, and as it is only necessary to detect the difference frequency signal in optical detector 107, it is appropriate to change either one of two light path lengths.

In reference system optical detector 108, signal 132 travelled through frequency shifter 104 and reflected at reference system reflector 105, and signal 128 reflected at reference system reflector 105, to be exact light signal which is the addition of amplitudes and phase of signals 132 and 128, are input. If two input signals of optical detector 108 are correlated, frequency difference signal 141 between two signals is output. The two input signals to optical detector 108 are both reflected by the same reference system reflector and are introduced to optical detector with the same light path lengths, resulting in continuously correlated M-series codes and output of frequency difference signal 141 between two signals from optical detector 108.

In measurement system optical detector 107, signal 131 reflected at reference system reflector 105 and travelled through frequency shifter 104, and signal 126 reflected and scattered at measurement object 106, to be exact light signal which is the addition of amplitudes and phase of signals 132 and 126, are input. If two input signals of optical detector 107 are correlated, frequency difference signal 140 between two signals is output. On the other hand, if two input signals of optical detector 107 are not correlated, only noise and direct current signal resulting from spectrally spread by ultrarapid M-sequence signal are detected.

Signals 140 and 141 output from two optical detectors 107 and 108 went through extraction of necessary frequency bandwidth (removal of DC component; n-times harmonics of frequency difference signal=100 MHz, i.e., shifted frequency by frequency shifter 107; and other noises) by filters 110 and 111, and then converted to digital signals by AD converters 112, 113. Demodulator 109 performs complex (IQ) demodulation of frequency difference signal 144 of measurement system generated by reflected light from measurement object, using reference signal of AD-converted difference signal 145 of reference system. In FIG. 1, a single demodulator 109 is used, but separate complex (IQ) demodulators for each of measurement system signal 144 and reference system signal 145 may be used so that both demodulated IQ signals be combined to extract the reflected signal at measurement object 106. The details are explained using FIG. 6. Incidentally, frequency difference signal 145 is identical to the frequency signal (for example 100 MHz) with which frequency shifter 107 converts, the excitation signal of frequency shifter 107 itself may be used. In this situation, the excitation signal of frequency shifter 107 itself may be used. In this situation, excitation signal of frequency shifter 107 may be input to AD converter 113 as a signal 143; optical detector 108 and filter 111 may be omitted.

Here IQ demodulator is constructed as a digital device, but analog type IQ demodulator may be used. In this constitution, sampling frequency of AD converters are considerably decreased and may be favorable if multiple optical detectors are implemented.

Fourier transformer 115 functions as an analyzing part to analyze reflection site and reflection intensity, and performs inverse Fourier transform of reflection site information obtained by demodulator 109, that is, frequency-domain spectrum to obtain reflection site and reflection intensity. More specifically, by discrete Fourier transform (DFT) or Fourier series expansion, reflection sites and reflection intensity at each of these are acquired. In case of discrete Fourier transform, further interpolation may be necessary.

Next, the constitution of light path length changing part 114 is explained. For light path length changing part, mirror with staircase patterned surface, light path having fibers of different effective lengths, mirror having movable function, etc. can be implemented.

FIG. 3 illustrates the concept of optical detector 107 and light path length changing part 114.

To each detection element (for example, photodiode) 1071 of optical detector 107, reflected light 106 by measurement object 106 and reflected light 133 by reference system reflector 105. In FIG. 3, light path length of reflected light 126 to each detection element 1071 is shown to be different just for illustration purpose, but the light path length form measurement object 106 to each detection element 1071 is actually the same.

Here, optical detector 107 is explained; optical detector 108, on the other hand, has the same constitution as optical detector 107 but light without passing light path length changing part 114 is introduced.

As previously stated, reflected light 133 by reference system reflector 105 contains light components with different light path lengths, light path length input to each detection element 1071 is different from others. In FIG. 3, the light path length to the leftward detection element 1071 is short, and the light path length to the rightward detection element 1071 is long.

By setting the difference in light path length to be shorter than one bit length of M-series code, autocorrelation of M-series code is obtained only by one particular detection element 1071, but no autocorrelation of M-series code is obtained by other detection elements 1071. By these methods, reflected light from measurement object 106 only in a particular range of depth (in a particular range of light path length) can be extracted.

The difference in light path length of each detection element 1071 may be changed according to the waveform of M-series code. That is, the light path length difference which does not skip the neighboring light pulse (i.e., delay time) may be used. More specifically, as stated in later Equation (12), summation range of correlation $S(\omega)$ ranges between r of $-CT/2$ to $CT/2$; at least one observation point is necessary within this range. Thus, the light path length difference of light path length changing part 114 has to be less than or equal to $C \times T/2$. For example, even with the half cycle shift of pulse waveforms of M-series code, if the M-code series can be partially overlapped, autocorrelation between codes can be obtained and the frequency difference signal is obtained with the magnitude depending on the degree of overlap (refer to FIG. 8(B)). On the other hand, if the M-code series cannot be overlapped with the half cycle shift of pulse waveforms of M-series code, autocorrelation between codes is not obtained and the frequency difference signal is not obtained (refer to FIG. 8(C)). These arguments indicate that light path length difference may be larger if the overlap between pulses is small, and that light path length difference may be smaller if the overlap between pulses is large.

By summing reflected light 126 from measurement object 106 and reflected light 133 from reference system reflector 105 at optical detector 107, signal with difference frequency between reflected light 126 and reflected light 133, and M-sequence code is convoluted with this difference frequency signal. Thus, if the bit position of M-sequence code in reflected light 126 and of M-sequence code in reflected 133 is the same, autocorrelation between the two M-series codes are obtained and the signal 140 of frequency difference and the corresponding phase is acquired as stated previously. On the other hand, if the bit position of M-sequence code in reflected light 126 and of M-sequence code in reflected 133 is different, autocorrelation between the two M-series codes are not obtained and noise level signal 140 is output from optical detector 107.

In these ways, each detection element 1071 of optical detector 107 can detect reflected light from measurement object 106 with different light path lengths, i.e., optical detector 107 can detect difference signal having amplitude and phase of light reflected at different depths of measurement object 106.

Output signal 140 from optical detector 107 has the unnecessary frequency components removed by filter 110, and is input to AD converter 112 as signal 142. AD converter 112 converts the input analog signal into digital signal 144, and inputs to IQ demodulator 109.

In addition, by summing reflected lights 128 and 132 from reference system reflector 105 at optical detector 108, signal with difference frequency between reflected light 128 and reflected light 132, and M-sequence code is convoluted with this difference frequency signal. In case of optical detector 108, the light path lengths are the same between reflected light 128 and reflected light 143, the bit position of M-sequence code in reflected light 128 and in reflected 132 is the same, autocorrelation between the two M-series codes are obtained and the signal 140 of frequency difference and the corresponding phase is acquired.

Output signal 141 from optical detector 108 has the unnecessary frequency components removed by filter 110, and is input to AD converter 113 as signal 143. AD converter 113 converts the input analog signal into digital signal 145, and inputs to IQ demodulator 109.

IQ demodulator 109 demodulates signal 145 which contains the components of reflected light from measurement object 106 using local oscillatory signal 145 which only contains the component of reflected light 145 from reference system reflector 105. Thus, by IQ demodulator 109, signals corresponding to the amplitude and phase of reflected light from different depths (positions described by light path lengths) of measurement object 106.

FIG. 4 illustrates a concrete example of constitution of light path length changing part 114.

As shown in FIG. 4, light path length changing part 114 comprises a mirror 1143 with surface patterned in a staircase manner to change the light path length of light reflected by reference system reflector 105.

Light introduced to light path length changing part 114 diverges by concave lens 1141, and then converges to be parallel by convex lens 1142 and reflects by mirror 1143. As the surface of mirror 1143 is patterned in a staircase manner, light reflected by each of step outputs light with different light path length.

Difference in light path length is defined by the lateral step size of the mirror surface shown in FIG. 4.

Light output from light path length changing part 114 is aligned with the pitch of detection elements 1071 of optical detector 107.

FIG. 5 illustrates another concrete example of constitution of light path length changing part 114.

Light path length changing part 114 shown in FIG. 5 changes light path length by using optical fibers 1147 with different lengths. Specifically, input light to light path length changing part 114 diverges at slab waveguide 1145, and is introduced to plural of optical fibers with different lengths. Light propagated in each optical fiber 1147 is condensed by slab waveguide 1146 to match the pitch of detector elements 1071 of optical detector 107, and output from light path length changing part 114.

Light path length changing part 114 in FIG. 5 changes light path length by different length of each optical fibers 1147, but some or all fiber 1147 length may be same but these light propagation speed within each optical fiber 1147 may be differently controlled by electrical field.

Furthermore, light path length changing part 114 may change light path length by moving a mirror.

FIG. 6 demonstrates a method to obtain the reflection site and reflection rate within measurement object 106 from output signal 140 from optical detector 107. In FIG. 6, both M-series codes contained in reference light 133 reflected from reference system reflector 105 and reflected light 126 from measurement object 106 are shown along time axis. Though reflected lights from multiple positions within measurement object are actually contained, only reflected light from a single point is used for convenience of explanation.

In measurement system optical detector 107, reference light 133 and reflected light 126 are originally the same signal but the reflection sites are different by r (the light path lengths by 2r) and signal phase differs by the difference in light path lengths. If reference light 133 and reflected light 126 are summed at optical detector 107, signal with carrier light frequency difference (100 MHz in this embodiment) convoluted by M-series code is output.

On the other hand, in reference system optical detector 108, reference light 132 and reference light 128 are originally the same signal and the reflection sites (the light path lengths) are the same. Therefore, if reference light 132 and reflected light 128 are summed at optical detector 107, signal with carrier light frequency difference (100 MHz in this embodiment) convoluted by M-series code is output.

Phase of frequency difference signal of reference system and phase of frequency difference signal of measurement system differs by $\varphi$. Using parameter of light path length difference 2r, $\varphi$ is expressed as $\varphi=2r\omega/c$ ($\omega$ is light frequency output from light source 100).

One detection element 1071 of optical detector 107 extracts only the light input to optical detector 107 at a particular timing due to the autocorrelation characteristic of M-series code. As light source 100 outputs light varying wave lengths, plurality of signals with different amplitude and phase at multiple frequencies are obtained. Because amplitude is determined by reflection rate at reflection site within measurement object 106 and phase is determined by light path length difference, collecting plural data sets of amplitude and phase and subjecting these to analysis enables calculation of reflection rate at each reflection sits.

Calculation methods explained above is explained using equations.

Let irradiated light to measurement object 106 be transmitted signal $x(\omega, t)$, and let reflected and scattered light from measurement object 106 be received signal $y(\omega, t)$. In the following calculation, autocorrelation is calculated for general signal but not limited to pulse train.

Transmitted signal $x(\omega, t)$ is expressed as Equation (1).

[Equation 1]

$$x(\omega, t) = \sum_{k=0}^{L-1} M(k) \cdot m(t-kT) \cdot \exp(j\omega t) \cdot f(t-kT) \quad (1)$$

Here a function expressing pulse waveform of M-series code is defined as function f(t) expressed as Equation (2).

[Equation 2]

$f(t) \neq 0: -T < t < T$ $f(t) = 0: t < -T \text{ or } T < t$ \quad (2)

If focused only on one bit of M-series signal, pulse of transmitted signal is expressed as Equation (3).

[Equation 3]

$x(\omega, t) = \exp(j\omega t) \cdot f(t)$ \quad (3)

Pulse of received signal is expressed as Equation (4).

[Equation 4]

$$y(\omega, t) = \int A(r) \cdot x\left(\omega, t - t_d - \frac{2r}{c}\right) dr \quad (4)$$

Reflection site of measurement object 106 is more distant by distance r compared to the reference system reflector 105. The position of reference system reflector 105 is described as (C·td)/2, and the position of measurement object 106 is described as r+(C·td)/2. If the reflection factor within the measurement object at position near (C·td)/2 is denoted as A(r), the correlation S(t) is expressed as Equations (5) and (6).

[Equation 5]
$$S(\omega) = \int y(t) \cdot \bar{x}(t - t_d) dt \tag{5}$$

[Equation 6]
$$\int S(\omega) = \int \left\{ \int A(r) \cdot \exp\left[j\omega \cdot \left(t - t_d - \frac{2r}{C}\right)\right] \cdot f\left(t - t_d - \frac{2r}{C}\right) dr \right\} \cdot \exp[-j\omega \cdot (t - t_d)] \cdot \bar{f}(t - t_d) dt$$
$$= \int A(r) \cdot \exp\left[j\omega \cdot \left(-\frac{2r}{C}\right)\right] \cdot \left[\partial f\left(t - t_d - \frac{2r}{C}\right) \cdot \bar{f}(t - t_d) dt\right] dr \tag{6}$$

Here, range of integration of Equation (6) is determined to finite range, by the range of r determined by the condition of Equation (7). Integration is calculated first in terms of t.

[Equation 7]
$$\int f\left(t - t_d - \frac{2r}{C}\right) \cdot \bar{f}(t - t_d) dt \neq 0 \tag{7}$$

[Equation 8]
$$\int_{-\infty}^{\infty} f\left(t - t_d - \frac{2r}{C}\right) \cdot \bar{f}(t - t_d) dt = \int_{-\frac{T}{2}}^{\frac{T}{2}} f\left(t - \frac{2r}{C}\right) \cdot \bar{f}(t) dt \tag{8}$$

Therefore, the range of r has to satisfy the condition of Equation (9), and Equation (9) can be converted to Equations (10) and (11). Furthermore, correlation S(t) is shown as Equation (12). T is the length of one bit of M-series code in the equations hereafter.

[Equation 9]
$$-\frac{T}{2} < t < \frac{T}{2}$$
$$-\frac{T}{2} < t - \frac{2r}{C} < \frac{T}{2}$$
$$-T < -\frac{2r}{C} < T \tag{9}$$

[Equation 10]
$$-T < -\frac{2r}{C} < T \tag{10}$$

[Equation 11]
$$-\frac{CT}{2} < r < \frac{CT}{2} \tag{11}$$

[Equation 12]
$$S(\omega) = \int_{-\frac{CT}{2}}^{\frac{CT}{2}} A(r) \cdot \exp\left[j\omega \cdot \left(-\frac{2r}{C}\right)\right] \cdot \left[\int_{-\frac{T}{2}}^{\frac{T}{2}} f\left(t - \frac{2r}{C}\right) \cdot \bar{f}(t) dt\right] dr \tag{12}$$

As the integration range of correlation S(ω) is finite, A(r) can be expressed in the form of Fourier series. Here ω is defined as in Equation (13), and a(r) as in Equation (14), correlation (n, ω) can be expressed as Equation (15).

[Equation 13]
$$\omega = \omega_0 + n \cdot \omega_s \tag{13}$$

[Equation 14]
$$a(r) \equiv A(r) \cdot \exp\left(j\omega_0 \cdot \frac{2r}{C}\right) \cdot \int_{-\frac{T}{2}}^{\frac{T}{2}} f\left(t - \frac{2r}{C}\right) \cdot \bar{f}(t) dt \tag{14}$$

[Equation 15]
$$S(n \cdot \omega_s) = \int_{-\frac{CT}{2}}^{\frac{CT}{2}} a(r) \cdot \exp\left[-h \cdot n \cdot \omega_s \cdot \left(-\frac{2r}{C}\right)\right] dr \tag{15}$$

Therefore, by making the cycle of exp[–j·ω_S·(–2r/C)]S be CT, FS coefficients of a(r) is obtained. Thus, ω_S is expressed as Equations (16) and (17), exp[–j·ω_S·(–2r/C)] and is expressed as Equation (18).

[Equation 16]
$$\omega_s \cdot \left(-\frac{2CT}{C}\right) = 2\pi \tag{16}$$

[Equation 17]
$$\omega_s = \frac{\pi}{T} \tag{17}$$

[Equation 18]
$$\exp\left[-j \cdot \omega_s \cdot \left(-\frac{2r}{C}\right)\right]_s = \exp\left[j \cdot \frac{2\pi r}{CT}\right] \tag{18}$$

Using these, correlation of each wave length (frequency) of light emitted by light source 101 is described by Equation (19) and FS coefficients of a(r) are obtained. Thus, a(r) is expressed as Equation (20).

[Equation 19]
$$S_n = S(n \cdot \omega_s) = \int_{-\frac{CT}{2}}^{\frac{CT}{2}} a(r) \cdot \exp\left[j \cdot \left(\frac{2r}{C}\right)\right] dr \tag{19}$$

[Equation 20]
$$a(r) = \frac{1}{CT} \sum_{n=-\infty}^{\infty} S_n \exp\left[j \cdot n \cdot \frac{2\pi r}{CT}\right] \tag{20}$$

By using previous Equation (14), reflection rate A(r) as a function of distance is obtained as shown in Equation (21).

[Equation 21]
$$|A(r)| = \frac{1}{\int_{-T/2}^{T/2} f\left(t - \frac{2r}{C}\right) \cdot \bar{f}(t) dt} |a(r)| \tag{21}$$

FIG. 7 illustrates the measurable range CT of reflection site by autocorrelation, and FIG. 8 shows signals output from optical detector.

Light reflected by reflector 105 at the position B in the Figure inputs to optical detector 107 with light path length of ABC. On the other hand, light reflected by measurement object 106 inputs to optical detector 107 with light path length of ADE. As stated earlier, if light path length is completely the same, M-series codes are correlated with each other for all the symbol length as shown in FIG. 7(A) and high-level frequency difference signal 140 is obtained as shown in FIG. 8(A).

In another case, if light path length difference is less than one bit width (CT) of M-series code as shown in FIG. 7(B), weak autocorrelation is obtained and low-level frequency difference signal 140 is obtained as shown in FIG. 8(B).

In still another case, if light path length difference is more than one bit width (CT) of M-series code as shown in FIG. 7(C), no autocorrelation is obtained between reflected light from reference system reflector 105 and reflected light from measurement object 106, and noise-level signal is obtained as shown in FIG. 8(C).

In the first embodiment, tomographic imaging device to measure one point in the direction of depth using optical detector 107 with detection elements 1071 aligned in one-dimensional (linear) manner; by placing multiple light sources 100 in a linear manner and using optical detector 107 with detection elements 1071 aligned in two-dimensional (planar) manner, two-dimensional tomographic image with depth direction is obtained. Furthermore, by placing multiple light sources 100 in a planar manner and using optical detector 107 with detection elements 1071 aligned in three-dimensional (volumetric) or two-dimensional (planar) manner, three-dimensional tomographic image with depth direction is obtained.

Next, the effect of tomographic imaging device according to the first embodiment is explained. FIG. 9 shows the simulation results within measurement range. In FIG. 9, reflection rate 900 of measurement object 106 is shown as a function of depth. Reflection rate 900 used in this simulation is set to lower values in the deeper part taking into account the decay of light along the light propagation within measurement object 106. Another line 901 shows the simulated imaging results of tomographic imaging device according to the first embodiment, and still another line 902 shows the simulated imaging results of conventional tomographic imaging device.

In FIG. 9, range 903 circumscribed by broken lines indicates the range in which autocorrelation according to M-series code can be obtained; in the first embodiment of tomographic imaging device, reflection rate of measurement object 106 can be obtained as a function of depth only within this range. More precisely, larger reflection rate is obtained in the center region of the range circumscribed by broken lines due to stronger correlation, and reflection rate becomes smaller in advancing to both sides. Knowing precise reflection rate requires the correction by the strength of correlation.

In the first embodiment of tomographic imaging device, by changing light path length difference sequentially, the range 903 with considerable autocorrelation is moved, and tomographic images in broad range of depth can be imaged.

In conventional tomographic imaging device, reflection from deeper part of measurement object 106 becomes weaker; refection is hidden in noise beyond certain point disabling the measurement refection deeper than this point. In contrast, in tomographic imaging device according to this embodiment, detailed image within a narrow range is obtained using the characteristic of autocorrelation of M-series code. Besides, by using reference light with different path lengths, tomographic images can be imaged in range broader than the range with considerable autocorrelation of M-series code.

Second Embodiment

FIG. 10 shows constitution of tomographic imaging device according to the second embodiment of this invention.

The second embodiment of tomographic imaging device contains light source 100, light pulse generator 101, modulator 103, frequency shifter 104, light path length changing part 114, optical detector 107, 108, filter 110, 111, AD converter 112, 113, demodulator 109, and Fourier transformer 115.

In the second embodiment, wave shaper 102 is not included and the presence of modulator 103 in the constitution is different from the first embodiment. In the second embodiment, only the difference from previous embodiment is explained, and the same constituents as in the previous embodiment are designated by the same signs and their explanations are skipped.

Modulator 103 in the second embodiment modulates the phase of signal 101 output from light pulse generator 101 according to M-series code, and outputs signal 123. In this embodiment, modulator 103 is constituted by LN modulator. LN modulator makes use of change in refractive index induced by Pockets effect of $LiNbO_3$ crystal, has the characteristic to output light with no applied voltage and to output no light with no applied voltage.

FIG. 11 illustrates an example of light output from modulator 103 in tomographic imaging device according to the second embodiment.

In the second embodiment, light pulse generator 101 converts the light (continuous light) generated by light source 100 to pulse light 122 with, for example, 40 µs intervals by controlling light amplitude by 25 GHz signal.

Modulator 103 modulates the phase of signal 101 output from light pulse generator 101 according to M-series code, and outputs signal 123. In this embodiment, modulator 103 is constituted by LN modulator.

In the second embodiment, frequency of input signal to modulator 103 is low, and modulation according to M-series is performed in a relatively slower speed. Therefore, modulator 103 may be constituted with cheap LN modulator and the cost of the device may be lowered.

Third Embodiment

FIG. 12 shows constitution of tomographic imaging device according to the third embodiment of this invention.

The third embodiment of tomographic imaging device contains light source 100, modulator 103, frequency shifter 104, light path length changing part 114, optical detector 107, 108, filter 110, 111, AD converter 112, 113, demodulator 109, and Fourier transformer 115.

In the third embodiment, light pulse generator 101 and wave shaper 102 is not included, and the presence of modulator 103 in the constitution is different from the first embodiment. In the third embodiment, only the difference from previous embodiments is explained, and the same constituents as in the previous embodiments are designated by the same signs and their explanations are skipped.

In the third embodiment, light pulse generator 101 and wave shaper 102 is not included. Modulator 103 in the third embodiment modulates the phase of continuous light input from light source 100 using M-series code, and outputs signal 123. In the third embodiment, modulator 103 is constituted by LN modulator similar as in the second embodiment.

FIG. 13 illustrates an example of light output from modulator 103 in tomographic imaging device according to the third embodiment.

In the third embodiment, light pulse generator 101 modulates the phase of the light (continuous light) generated by light source 100 according to, for example, M-series code of 25 GHz. Thus, the output of modulator 103 is not a pulse train but may be continuous (does not become zeroes if the same codes continue).

In the third embodiment, frequency of input signal to modulator 103 is low, and modulation according to M-series is performed in a relatively slower speed. Therefore, modulator 103 may be constituted with cheap LN modulator and the cost of the device may be lowered.

To this point, tomographic imaging device which extracts reflection light from a particular depth using measurement with multiple frequencies is explained; extraction of reflected light from a particular depth using confocal optical system may be used.

In the aforementioned paragraphs, this invention is explained in details in reference to the attached illustrations; this invention, however, is not limited to the above specific constitutions, but includes various modifications and similar constitutions within the intent of attached claims.

By referring their contents, this application includes Japanese Patent Application No. 2016-6210 applied on Jan. 15, 2016 and International Application PCT/JP 2017/26091 applied on Jul. 19, 2017.

The invention claimed is:

1. A tomographic imaging device, comprising:
a light source;
a light pulse generator which is configured to generate an optical pulse train from light output from the light source;
a wave shaper which is configured to modulate the optical pulse train by binary phase shift keying with a pseudo random (PN) code to output a modulated optical pulse train having pulses corresponding to bits of the pseudo random (PN) code;
a splitter which is configured to split the modulated optical pulse train into a first pulse train and a second pulse train;
a frequency shifter which is configured to shift a frequency of one of the first and second pulse trains to generate frequency shifted light;
a light path length changing part which is configured to change a light path length of one of the first and second pulse trains;
a first optical detector configured to receive a portion of the frequency shifted light that has been reflected by a reference system reflector and a portion of non-frequency shifted light that has been reflected by the reference system reflector, and output a first difference signal; and
a second optical detector configured to receive the one of the first and second pulse trains output from the light path changing part, and a back scattered wave of the other one of the first and second pulse trains that has been irradiated on the object to be measured, and output a difference signal indicating a difference between the input signals;
first filters which are configured to filter a difference signal between signals output from the frequency shifter that have a shift frequency of the frequency shifter;
second filters which are configured to filter a difference signal between two reference signals synchronized with the first and second pulse trains;
a demodulator which is configured to combine the difference signals filtered by the first and second filters; and
an analyzing part which is configured to analyze the output signal of the demodulator; and calculate a reflection site of the measurement object by analyzing the output signal of the demodulator.

2. A tomographic imaging device according to claim 1, wherein:
the wave shaper is configured to spectrally decompose the optical pulse train generated by the light pulse generator, adjust a phase and amplitude of each spectrum of the optical pulse train, and spectrally combine the adjusted optical pulse train, thereby reshaping and duplicating the optical pulse train.

3. A tomographic imaging device according to claim 2, wherein:
the wave shaper outputs the optical pulse train with each pulse of the optical pulse train not interfering and being independent from each other.

4. A tomographic imaging device according to claim 3, wherein:
the wave shaper reshapes the optical pulse train to a Chebyshev-type wave form and outputs the optical pulse train.

5. A tomographic imaging device according to claim 2, wherein:
the wave shaper is a spatial light modulator.

6. A tomographic imaging device according to claim 1, wherein:
the light pulse generator is configured to generate cyclical pulse light with a specified time width and repeating at a fixed time interval from the continuous light beam emitted by the light source.

7. A tomographic imaging device according to claim 1, wherein:
the light source changes a light wave length digitally to measure reflection site and reflection intensity from measured reflection wave phase and amplitude information;
the light path length changing part generates light with an altered light path length without intervening space between neighboring pulse light when different pulse lights reflected by a reference system reflector through the frequency shifter are aligned in a time axis;
the optical detection part includes a plurality of first optical detectors and plurality of first analog-to-digital (AD) converters;
and each detection element of the first optical detectors receives each of a plurality of the lights with altered light path length.

8. A tomographic imaging device according to claim 1, wherein:
the light source changes a light wave length during intervals between a time width T of a pulse of the optical pulse train;

the light path changing part generates light with an altered light path length in a step shorter than or equal to C×T/2 where C is a light speed within a measurement object;

the optical detection part includes a plurality of first optical detectors and plurality of first analog-to-digital (AD) converters;

and each detection element of the first optical detectors receives each of a plurality of the lights with altered light path length.

9. A tomographic imaging device comprising:

a light source;

a light pulse generator which is configured to generate pulsed light having pulses of a predetermined width and at a constant interval;

a wave shaper which is configured to modulate the pulsed light by binary phase shift keying with a pseudo random (PN) code to output a modulated pulsed light having pulses corresponding to bits of the pseudo random (PN) code within the constant interval;

a first splitter which is configured to split the modulated pulsed light into a first pulse signal and a second pulse signal;

a second splitter which is configured to split the second pulse signal into a third pulse signal and a fourth pulse signal;

a frequency shifter which is configured to shift a frequency of the first pulse signal and output a frequency shifted pulse signal;

a reference system reflector which is configured to reflect the frequency shifted pulse signal and the third pulse signal;

a light path length changing part which is configured to change a light path length of the reflected frequency shifted pulse signal;

a first optical detector configured to receive the reflected frequency shifted pulse signal and the reflected third pulse signal and output a first difference signal;

a second optical detector configured to receive the output of the light path length changing part and the fourth pulse signal which has been reflected from a measurement object, and output a second difference signal;

a first filter configured to filter the first difference signal;

a second filter configured to filter the second difference signal;

a demodulator configured to combine the filtered first and second difference signals; and an analyzing part configured to analyze an output signal of the demodulator to obtain a reflection site and a reflection intensity of the of the measurement object.

10. The tomographic imaging device according to claim 9, wherein the light path changing part changes the light path length by a length shorter than one bit length of the to select a pulse corresponding to a bit of the pseudo random (PN) code to select reflected light from the measurement of object in a particular range of depth.

* * * * *